(12) United States Patent
Ikawa et al.

(10) Patent No.: US 9,176,077 B2
(45) Date of Patent: Nov. 3, 2015

(54) HOLDING APPARATUS AND X-RAY DIAGNOSTIC APPARATUS

(71) Applicants: Katsuie Ikawa, Nasushiobara (JP); Masaki Kobayashi, Otawara (JP); Hajime Yoshida, Nasushiobara (JP); Satoshi Yamashita, Utsunomiya (JP)

(72) Inventors: Katsuie Ikawa, Nasushiobara (JP); Masaki Kobayashi, Otawara (JP); Hajime Yoshida, Nasushiobara (JP); Satoshi Yamashita, Utsunomiya (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 377 days.

(21) Appl. No.: 13/692,082

(22) Filed: Dec. 3, 2012

(65) Prior Publication Data
US 2013/0148783 A1 Jun. 13, 2013

(30) Foreign Application Priority Data
Dec. 9, 2011 (JP) .................................. 2011-270319

(51) Int. Cl.
| | | |
|---|---|---|
| A61N 5/10 | (2006.01) | |
| G01N 23/04 | (2006.01) | |
| G03B 42/02 | (2006.01) | |
| F16M 11/04 | (2006.01) | |
| F16M 11/10 | (2006.01) | |
| F16M 11/18 | (2006.01) | |
| A61B 6/00 | (2006.01) | |

(52) U.S. Cl.
CPC *G01N 23/04* (2013.01); *A61B 6/44* (2013.01); *A61B 6/4441* (2013.01); *F16M 11/043* (2013.01); *F16M 11/10* (2013.01); *F16M 11/18* (2013.01); *G03B 42/02* (2013.01)

(58) Field of Classification Search
CPC .. A61B 6/4429; A61B 6/4441; A61N 5/1081; G01N 23/04; G03B 42/02; F16M 11/043
See application file for complete search history.

(56) References Cited

U.S. PATENT DOCUMENTS

| 5,050,204 A * | 9/1991 | Siczek et al. ................... 378/197 |
|---|---|---|
| 5,912,943 A * | 6/1999 | Deucher et al. ............... 378/167 |
| 6,599,017 B2 * | 7/2003 | Geelhoed et al. ............... 384/58 |
| 6,789,941 B1 * | 9/2004 | Grady ........................... 378/197 |
| 2007/0280426 A1 * | 12/2007 | Saffer ............................ 378/198 |
| 2015/0010131 A1 * | 1/2015 | Arisaka et al. ................ 378/197 |

FOREIGN PATENT DOCUMENTS

JP 2010-240254 10/2010

* cited by examiner

*Primary Examiner* — Brooke Purinton
(74) *Attorney, Agent, or Firm* — Oblon, McClelland, Maier & Neustadt, L.L.P.

(57) ABSTRACT

According to one embodiment, a holding apparatus includes an arcuated arm, a first roller, and a second roller. The arcuated arm is provided with a guide groove along the outer surface, has a hollow portion inside, and holds the X-ray generator and X-ray detector while making them squarely face each other. The first roller runs in the hollow portion in contact with the inner wall of the hollow portion on the outer surface side. The second roller runs in the guide groove while being fitted in the guide groove, and holds the arm together with the first roller so as to allow the arm to slide along the arcuated direction.

4 Claims, 7 Drawing Sheets

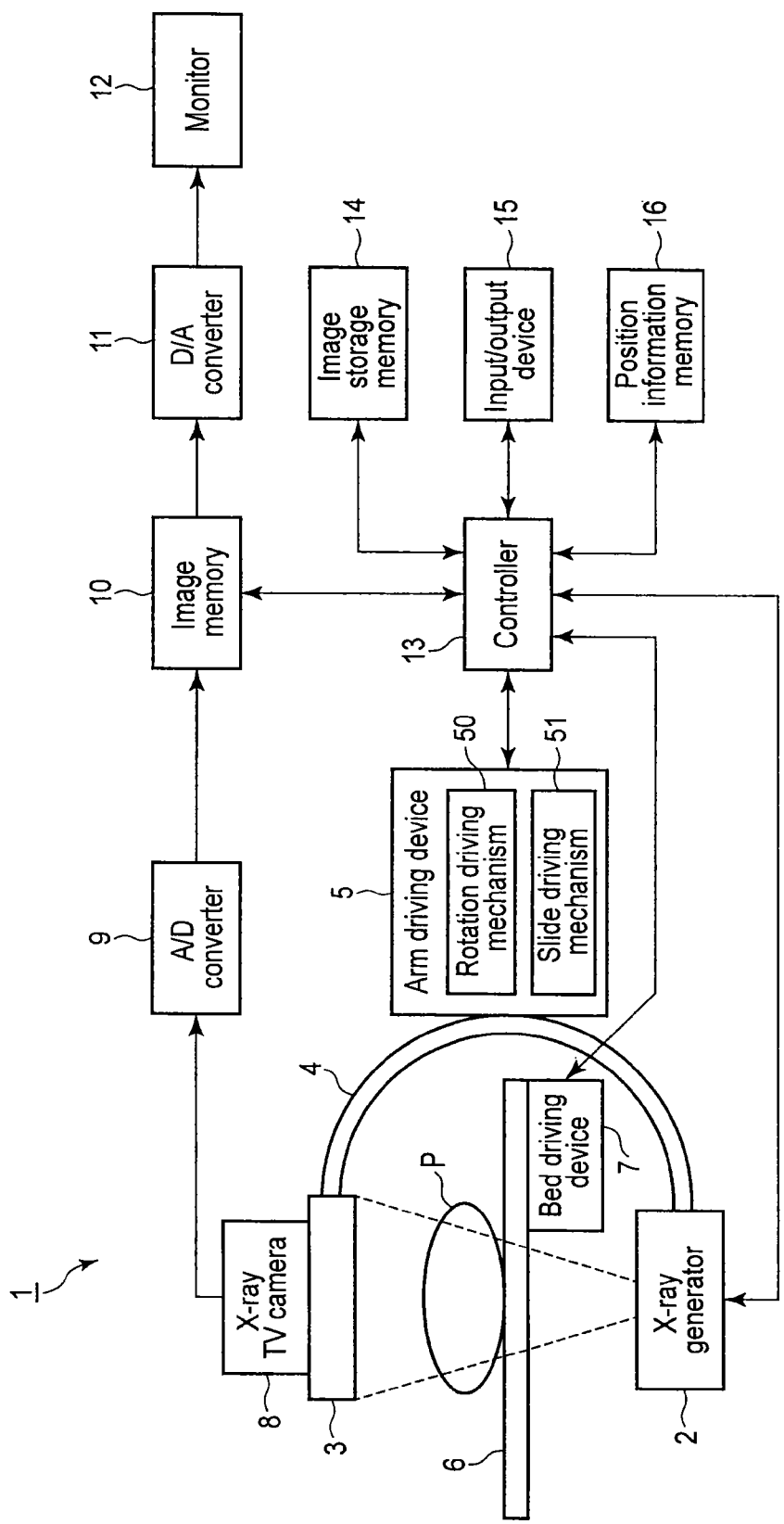
F I G. 1

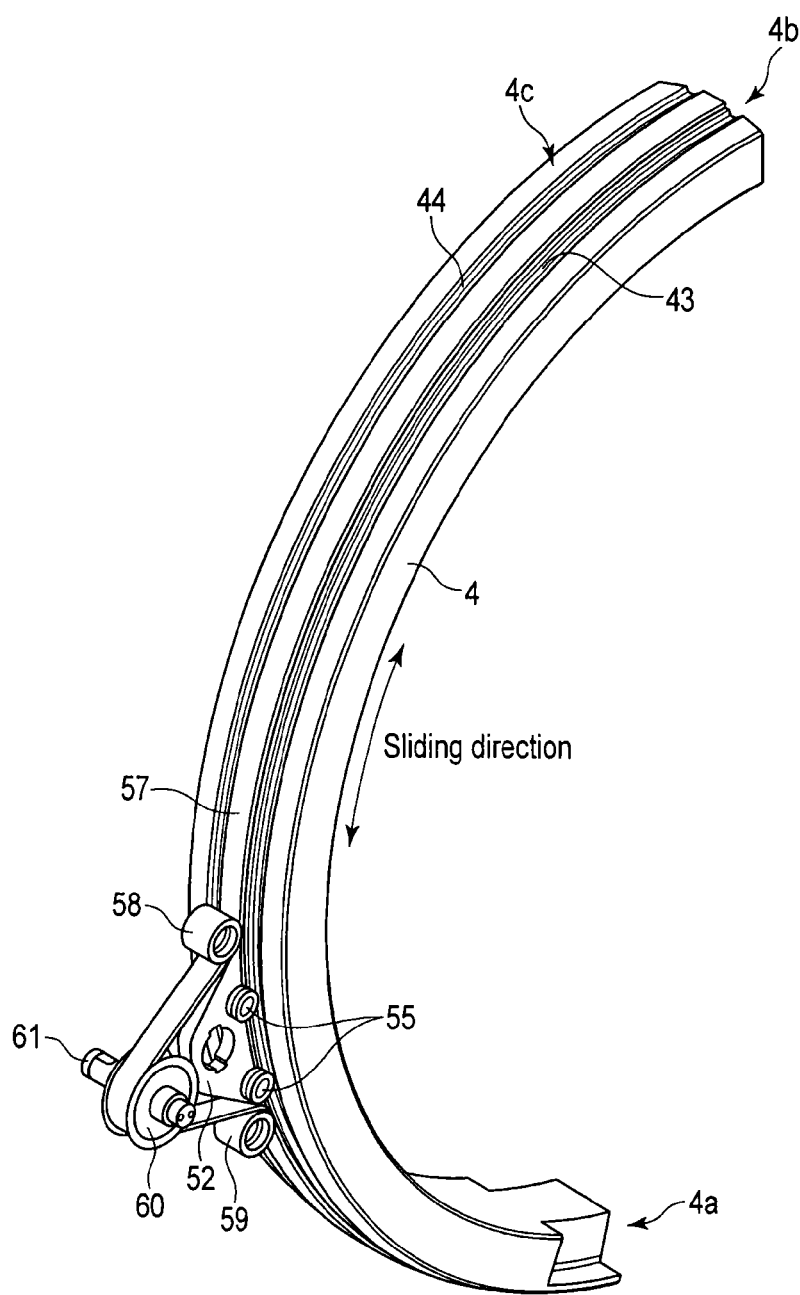
F I G. 2

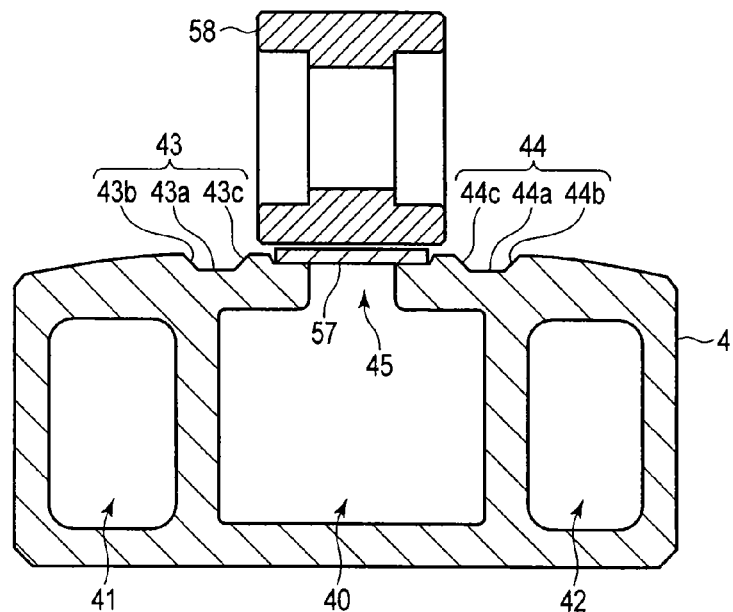
F I G. 4
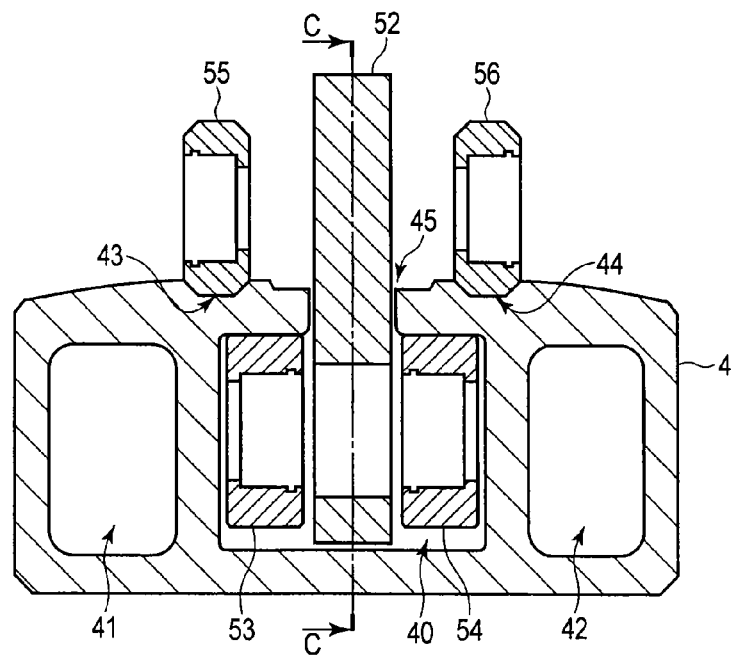
F I G. 5

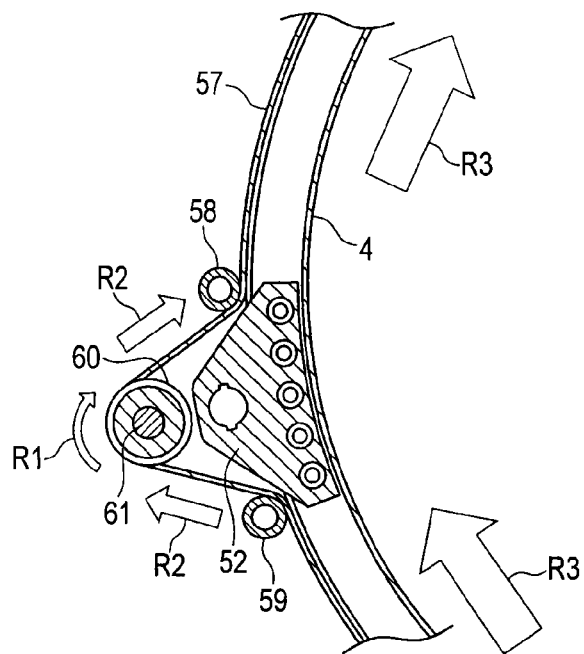
F I G. 7
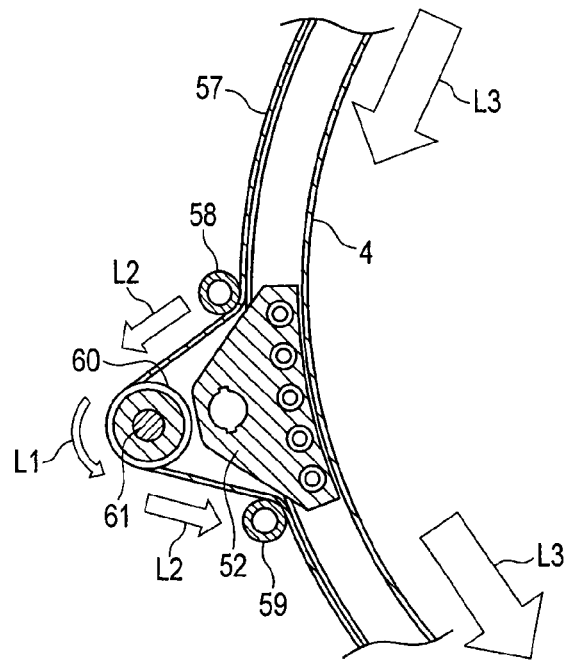
F I G. 8

US 9,176,077 B2

HOLDING APPARATUS AND X-RAY DIAGNOSTIC APPARATUS

CROSS-REFERENCE TO RELATED APPLICATIONS

This application is based upon and claims the benefit of priority from Japanese Patent Application No. 2011-270319, filed Dec. 9, 2011, the entire contents of which are incorporated herein by reference.

FIELD

Embodiments described herein relate generally to a holding apparatus and an X-ray diagnostic apparatus.

BACKGROUND

An X-ray diagnostic apparatus is an apparatus which irradiates an object with X-rays from an X-ray source, captures via an X-ray detector the X-rays transmitted through the object, and generates an X-ray transmission image which is a shadowgram proportional to the transit dose. The X-ray source and X-ray detector described above are held by a holding apparatus having an arm such as a C-arm or Ω-arm so as to squarely face each other. This arrangement allows to capture X-ray images of an object from various angles.

Conventionally, there are separately provided an operating room and a catheter room in which intervention (intravascular treatment) is performed using an X-ray diagnostic apparatus. If, therefore, it is necessary to perform surgery during the execution of intervention, the patient needs to be moved from the catheter room to the operating room.

Recently, providing, for example, an operating room with an X-ray diagnostic apparatus including the above holding apparatus which runs on the ceiling implements an environment which allows a vascular surgeon and a circulatory physician to cooperatively treat a circulatory disease. This eliminates the necessity to move the patient between the operating room and the catheter room, and allows to perform a speedy treatment. Such a system is called Hybrid OR System.

A room for Hybrid OR System differs in layout from a catheter room specified for intervention, and is provided with various types of apparatuses and tools, which limit the available space. It is therefore necessary for an X-ray diagnostic apparatus installed in this room, especially the above holding apparatus which is often located near a patient or an operator, to have a shape that does not interfere with the operator. In addition, the room for Hybrid OR System is sometimes used for surgery, and hence needs to be kept clean. However, a contrast medium and blood adhere to the above holding apparatus for the X-ray diagnostic apparatus during surgeries. In this regard, therefore, it is difficult to keep the above holding apparatus clean.

Under such a situation, it is necessary to downsize the above holding apparatus or the X-ray diagnostic apparatus and improve the cleanliness of the apparatuses.

BRIEF DESCRIPTION OF THE DRAWINGS

FIG. 1 is a block diagram showing the arrangement of the main part of an X-ray diagnostic apparatus according to an embodiment;

FIG. 2 is a perspective view showing part of a C-arm and slide driving mechanism according to this embodiment;

FIG. 4 is a sectional view taken along A-A of each element shown in FIG. 3;

FIG. 5 is a sectional view taken along B-B of each element shown in FIG. 3;

FIG. 7 is a view for explaining sliding operation according to this embodiment;

FIG. 8 is a view for explaining sliding operation according to this embodiment.

DETAILED DESCRIPTION

Figure 3:
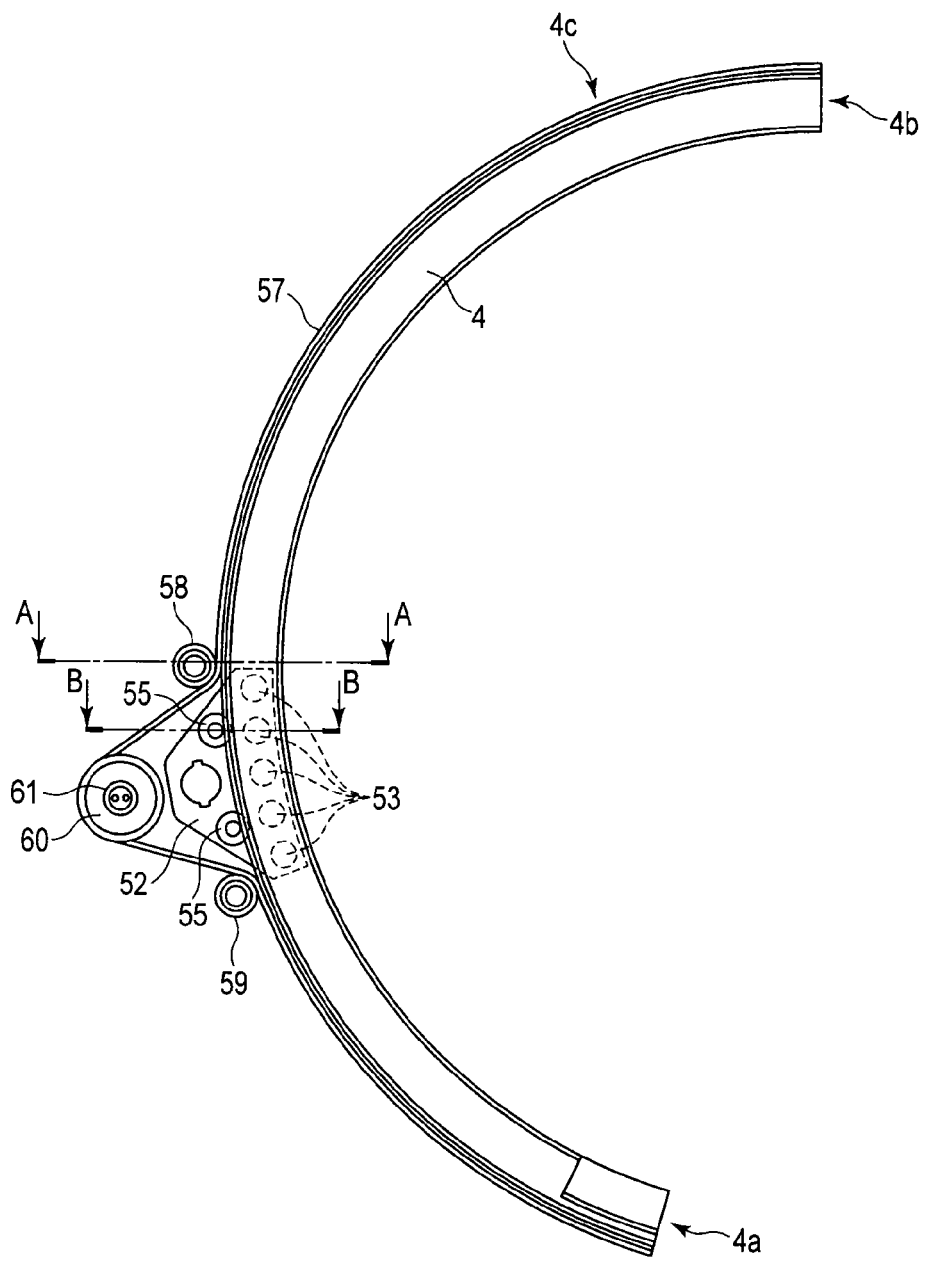
FIG. 3 is a side view of each element shown in FIG. 2.

In general, according to one embodiment, a holding apparatus includes an arcuated arm, a first roller, and a second roller.

The arcuated arm is provided with a guide groove along the outer surface, has a hollow portion inside, and holds the X-ray generator and X-ray detector while making them squarely face each other. The first roller runs in the hollow portion in contact with the inner wall of the hollow portion on the outer surface side. The second roller runs in the guide groove while being fitted in the guide groove, and holds the arm together with the first roller so as to allow the arm to slide along the arcuated direction.

An embodiment will be described with reference to the accompanying drawing.

The same reference numerals denote the same constituent elements in the following description, and a repetitive description will be omitted.

As an X-ray diagnostic apparatus according to this embodiment, an X-ray diagnostic apparatus 1 for circulatory organs, which can display captured images in real time will be described. FIG. 1 is a block diagram showing the arrangement of the main part of the X-ray diagnostic apparatus 1.

As shown in FIG. 1, the X-ray diagnostic apparatus 1 includes an X-ray generator 2, an X-ray detector 3, a C-arm 4, an arm driving device 5, a bed 6, a bed driving device 7, an X-ray TV camera 8, an A/D converter 9, an image memory 10, a D/A converter 11, a monitor 12, a controller 13, an image storage memory 14, an input/output device 15, and a position information memory 16.

The X-ray generator 2 includes an X-ray tube as an X-ray source, a stop which limits the irradiation range of X-rays, and a high voltage generator which generates X-rays by applying a high voltage to the X-ray tube. The X-ray detector 3 includes an image intensifier which converts the X-rays transmitted through an object P laid on the bed 6 into an optical image. Note that it is possible to use a flat panel detector instead of the image intensifier.

The C-arm 4 holds the X-ray generator 2 and the X-ray detector 3 so as to make the X-ray emitting surface of the X-ray generator 2 squarely face the X-ray detection surface of the X-ray detector 3. The arm driving device 5 drives the C-arm 4 so as to radiograph various regions of the object P from various angles.

The arm driving device 5 includes a rotation driving mechanism 50 for performing the main rotating operation (LAO/RAO) of rotating the C-arm 4 around the body axis of the object P and a slide driving mechanism 51 which slides the C-arm 4 in the sliding direction shown in FIG. 2 (to be described later) (CRA/CAU). The bed driving device 7 drives the bed 6 in the body axis direction of the object P and the lateral direction of the object P.

The X-ray TV camera 8 converts the optical image received by the X-ray detector 3 into an analog video signal, and outputs the video signal to the A/D converter 9. The A/D converter 9 converts the analog video signal input from the X-ray TV camera 8 into a digital video signal, and outputs it to the image memory 10. The image memory 10 stores the X-ray image (digital angiography) indicated by the digital video signal input from the A/D converter 9, together with the information (image accessory information) accessory to the acquisition of the X-ray image. The D/A converter 11 converts a digital video signal corresponding to the X-ray image stored in the image memory 10 into an analog video signal and outputs it to the monitor 12. The monitor 12 displays the X-ray image or the like based on the analog video signal input from the D/A converter 11.

The controller 13 includes a CPU (Central Processing Unit), a ROM (Read Only Memory), and a RAM (Random Access Memory). The controller 13 controls each unit of the X-ray diagnostic apparatus 1. In addition, the controller 13 performs various types of image processing for an X-ray image.

The image storage memory 14 acquires X-ray images stored in the image memory 10 and accumulates/stores X-ray images corresponding to many frames. The position information memory 16 stores the position of the bed 6 in the body axis direction at the time of capturing the X-ray image stored in the image memory 10, and position information such as the main rotational angle and slide angle of the C-arm 4.

The input/output device 15 includes a mouse, keyboard, buttons, trackball, joystick, and foot switch which are used by the operator such as a doctor who operates the X-ray diagnostic apparatus 1 to input various kinds of commands and information, and outputs the commands and information input by the devices to the controller 13. For example, at the time of diagnosis, the controller 13 selects an arbitrary image from the images stored in the image storage memory 14 in accordance with the instruction input from the input/output device 15, and reads out the selected image from the image memory 10. The monitor 12 displays the image read to the image memory 10.

The C-arm 4 and the slide driving mechanism 51 as part of the arm driving device 5 will be described next.

Figure 6:
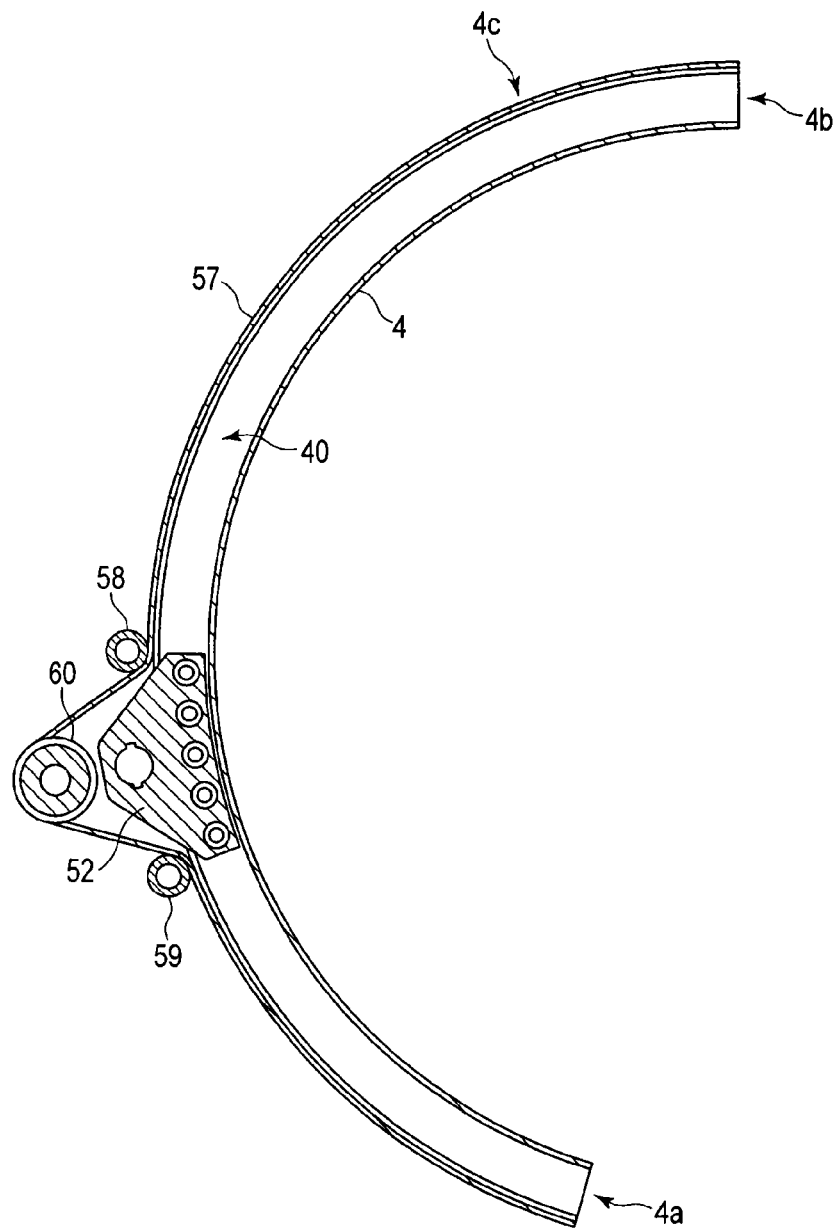
FIG. 6 is a sectional view taken along C-C of each element shown in FIG. 5.
Figure 9A:
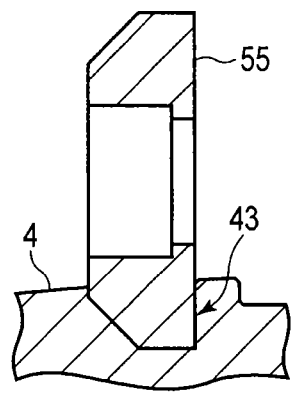
FIGS. 9A, 9B, 9C and 9D show guide grooves and wobbling prevention rollers according to a modification.
Figure 9B:
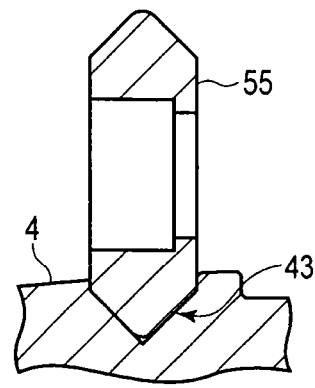
Figure 9C:
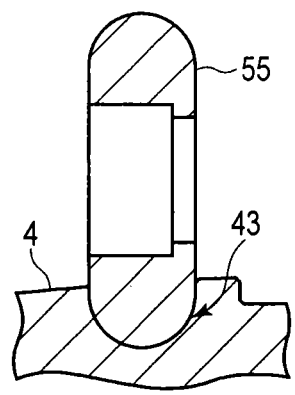
Figure 9D:
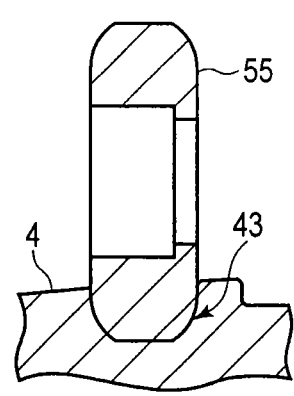

FIG. 2 is a perspective view showing part of the C-arm 4 and slide driving mechanism 51. FIG. 3 is a side view of each element shown in FIG. 2. FIG. 4 is a sectional view taken along A-A in FIG. 3. FIG. 5 is a sectional view taken along B-B in FIG. 3. FIG. 6 is a sectional view taken along C-C in FIG. 5.

As shown in FIG. 2, the C-arm 4 has an arcuated shape. The X-ray generator 2 and the X-ray detector 3 are respectively mounted on end portions 4a and 4b of the C-arm 4 such that the X-ray emitting surface of the X-ray generator 2 squarely faces the X-ray detection surface of the X-ray detector 3. As shown in FIG. 4, hollow portions 40, 41, and 42 are provided in the C-arm 4 throughout the total length of the C-arm 4.

An outer surface 4c of the C-arm 4 is provided with guide grooves 43 and 44 extending parallelly to each other throughout the total length of the outer surface. As shown in FIG. 4, the guide groove 43 is constituted by a bottom portion 43a and inclined portions 43b and 43c provided on the left and right sides of the bottom portion 43a. Likewise, the guide groove 44 is constituted by a bottom portion 44a and inclined portions 44b and 44c provided on the left and right sides of the bottom portion 44a. The outer surface 4c of the C-arm 4 is provided with an opening portion 45 extending between the guide grooves 43 and 44 parallelly to them throughout the total length of the outer surface and communicating with the hollow portion 40.

Part of a support frame 52 included in the slide driving mechanism 51 is inserted into the hollow portion 40 through the opening portion 45. At the portion of the support frame 52 which is inserted into the hollow portion 40, as shown in FIGS. 3 and 5, five pairs of left and right support rollers 53 and 54 (first rollers) are axially supported so as to be pivotal through bearings. The outer surfaces of the support rollers 53 and 54 of each pair abut against the inner wall of the hollow portion 40 on the outer surface 4c side, as shown in FIG. 5. In this state, each of the support rollers 53 and 54 runs in the hollow portion 40. Each drawing omits the illustration of the rotating shafts and the like of the support rollers 53 and 54 of each pair.

As shown in FIGS. 2, 3, and 5, two pairs of left and right wobbling prevention rollers 55 and 56 included in the slide driving mechanism 51 abut against the guide grooves 43 and 44. The wobbling prevention rollers 55 and 56 are axially supported so as to be pivotal through a support mechanism (not shown) included in the slide driving mechanism 51 so as to maintain the relative positional relationship with the support frame 52. Note that each drawing omits the illustration of the support mechanism and the like of the support rollers 53 and 54 of each pair. As shown in FIG. 5, the left and right edge portions of the outer surfaces of the wobbling prevention rollers 55 and 56 of each pair are chamfered so as to have shapes fitted in the guide grooves 43 and 44, respectively. The wobbling prevention rollers 55 and 56 of each pair run in the guide grooves 43 and 44 while being fitted in the guide grooves 43 and 44, respectively.

As described above, the C-arm 4 is held by the support rollers 53 and 54 of each pair arranged in the hollow portion 40 and the wobbling prevention rollers 55 and 56 of each pair arranged on the outer surface 4c side. This allows the C-arm 4 to slide in the sliding direction (the arcuated direction of the C-arm 4) indicated by the arrow in FIG. 2.

A mechanism for sliding the C-arm 4 will be described next. This mechanism includes a slide belt 57, slide belt rollers 58 and 59, a slide belt driving pulley 60 (driving member), a sliding power transmission key 61, a power source (a motor, servo amplifier, and like) (not shown), and a power transmission mechanism (speed reduction mechanism), all of which are included in the slide driving mechanism 51.

As shown in FIGS. 2 and 4, the slide belt 57 is stretched along the outer surface 4c. One end of the slide belt 57 is fixed to the C-arm 4 at a position near the end portion 4a of the C-arm 4, and the other end is fixed to the C-arm 4 at a position near the end portion 4b of the C-arm 4. The slide belt 57 closes the opening portion 45 except for the portion in which the support frame 52 is inserted. The width of the slide belt 57 is larger than that of the opening portion 45.

The slide belt rollers 58 and 59 are provided on the two sides of a protruding portion from the opening portion 45 of the support frame 52 on the moving path of the protruding portion when the C-arm 4 slides. More specifically, the slide belt roller 58 presses the slide belt 57 against the outer surface 4c at a position near one end of the protruding portion from the opening portion 45 of the support frame 52, whereas the slide belt roller 59 presses the slide belt 57 against the outer surface 4c at a position near the other end of the protruding portion.

Note that the slide belt rollers 58 and 59 are axially supported so as to be pivotal through a support mechanism (not shown) included in the slide driving mechanism 51 and maintain the relative positional relationship with the support frame 52. Each drawing omits the illustration of the support mechanism and the like for the slide belt rollers 58 and 59.

The slide belt driving pulley 60 is provided above protruding portion from the opening portion 45 of the support frame 52. The entire outer surface of the slide belt driving pulley 60 is provided with teeth at a predetermined pitch. The sliding power transmission key 61 is the rotating shaft of the slide belt driving pulley 60.

The sliding power transmission key 61 is rotated/driven by the power transmitted from the power source through the power transmission mechanism. As the sliding power transmission key 61 rotates, the slide belt driving pulley 60 rotates. The portion of the slide belt 57 which is located between the slide belt rollers 58 and 59 is wound around the slide belt driving pulley 60, as shown in FIG. 2 or the like. This makes the slide belt 57 between the slide belt rollers 58 and 59 straddle the protruding portion of the support frame 52, while the remaining portions of the slide belt 57 come into tight contact with the outer surface 4*c* to close the opening portion 45.

The lower surface of the slide belt 57 (the surface in contact with the slide belt driving pulley 60) is provided with straight teeth meshing with the teeth of the slide belt driving pulley 60 throughout the total length. As the slide belt driving pulley 60 rotates, the slide belt 57 is fed out in the rotating direction. Note that the sliding power transmission key 61 is supported by the above power transmission mechanism and other support mechanisms so as to maintain the relative positional relationship with the slide belt driving pulley 60 and the support frame 52. Each drawing omits the illustration of the mechanism for supporting the sliding power transmission key 61.

The operation of the above arrangement will be described next.

When the slide belt driving pulley 60 remains at rest, the position of the C-arm 4 relative to the support frame 52 (or the slide driving mechanism 51) is fixed with the tensile force and the like of the support rollers 53 and 54 of each pair, the wobbling prevention rollers 55 and 56 of each pair, and the slide belt 57.

As shown in FIG. 7, as the slide belt driving pulley 60 is rotated in the direction of an arrow R1, the slide belt 57 is fed from the end portion 4*a* side of the C-arm 4 to the end portion 4*b* side as indicated by an arrow R2. Along with this operation, the end portion 4*a* of the C-arm 4 is pulled. At this time, the support rollers 53 and 54 of each pair and the wobbling prevention rollers 55 and 56 rotate in contact with the inner wall of the hollow portion 40 on the outer surface 4*c* side and the guide grooves 43 and 44, and the C-arm 4 slides in the direction of an arrow R3 relative to the support frame 52 (or the slide driving mechanism 51).

On the other hand, as shown in FIG. 8, as the slide belt driving pulley 60 is rotated in the direction of an arrow L1, the slide belt 57 is fed from the end portion 4*b* side of the C-arm 4 to the end portion 4*a* side, as indicated by an arrow L2. Along with this operation, the end portion 4*b* of the C-arm 4 is pulled. At this time, the support rollers 53 and 54 of each pair and the wobbling prevention rollers 55 and 56 rotate in contact with the inner wall of the hollow portion 40 on the outer surface 4*c* side and the guide grooves 43 and 44, and the C-arm 4 slides in the direction of an arrow L3 relative to the support frame 52 (or the slide driving mechanism 51).

When the C-arm 4 slides, it swings and wobbles in various directions due to its own weight and the like. This may lead to the inability to stably capture X-ray images. Especially when performing so-called road map imaging of superimposing and displaying, on the monitor 12, X-ray images obtained in real time and images such as blood vessel images obtained in advance, the above swinging and wobbling greatly affect diagnosis. In this regard, this embodiment provides the guide grooves 43 and 44 and the wobbling prevention rollers 55 and 56, each having the shape described above, and hence suppresses swinging and wobbling in the direction in which the bottom surfaces 43*a* and 44*a* of the guide grooves 43 and 44 come into contact with the outer surfaces of the wobbling prevention rollers 55 and 56 of each pair (the vertical direction in FIG. 5), the direction perpendicular to it (the lateral direction in FIG. 5), and intermediate directions between the respective directions. Therefore, since the C-arm 4 stably slides, the X-ray diagnostic apparatus 1 can obtain good X-ray images.

Note that the slide driving mechanism for a conventional general X-ray diagnostic apparatus for circulatory organs has, for example, guide grooves on the two side surfaces of a C-arm, and holds the C-arm by attaching side rollers to the respective guide grooves by pressure. This arrangement leads to an increase in the size of the slide driving mechanism in the widthwise direction of the C-arm (corresponding to the lateral direction in FIG. 5). In contrast to this, the arrangement of supporting the C-arm 4 from the inside of the hollow portion 40 as in this embodiment allows to effectively use a dead space in the C-arm 4. It is therefore not necessary to provide any mechanism for supporting the C-arm 4 on the side surface of the C-arm unlike the prior art. This can therefore downsize the holding apparatus constituted by the C-arm 4, the arm driving device 5, and the like or the X-ray diagnostic apparatus 1.

In addition, using an arrangement configured to support a C-arm by using side rollers in guide grooves on the two side surfaces of the arm, like the conventional slide driving mechanism described above, may make scattering contaminants such as a contrast medium and blood during surgery on a patient adhere to portions from which it is difficult to remove, such as the guide grooves and side rollers on the two side surfaces, resulting in contaminating the apparatus. In contrast to this, using a mechanism configured to support the C-arm 4 from the inside of the hollow portion 40, like this embodiment, eliminates the necessity to provide any mechanisms for supporting the C-arm 4 on the side surfaces of the C-arm 4 as in the related art. This makes it difficult for contaminants such as a contrast medium and blood to adhere to the mechanism for sliding the C-arm 4. Even if contaminants adhere to the C-arm 4, it is possible to easily wipe them off. In addition, the opening portion 45 of the C-arm 4 is mostly closed by the slide belt 57. This can prevent contaminants from entering the hollow portion 40.

As described above, the arrangement of the holding apparatus and X-ray diagnostic apparatus 1 according to this embodiment greatly improves cleanliness as compared with the conventional structure.

In addition, the arrangement of this embodiment can obtain various preferable effects.

Note that the arrangement disclosed in the above embodiment can be variously modified and implemented.

For example, the above embodiment has exemplified the X-ray diagnostic apparatus 1 including the C-arm 4. However, the X-ray diagnostic apparatus 1 may include an arm having other shape like an Ω-arm instead of the C-arm 4. A mechanism similar to that for the C-arm 4 in the above embodiment can also be provided for arms having other shapes.

In addition, the above embodiment includes the guide grooves 43 and 44 having the shapes shown in FIG. 5 and like and the wobbling prevention rollers 55 and 56 having the outer surface shapes conforming to them. However, the guide grooves 43 and 44 and the outer surfaces of the wobbling prevention rollers 55 and 56 may have other shapes as long as they can prevent swinging and wobbling in the direction in which the guide grooves 43 and 44 come into contact with the wobbling prevention rollers 55 and 56 of each pair (the vertical direction in FIG. 5), the rotational axis direction of the wobbling prevention rollers 55 and 56 (the lateral direction in FIG. 5), and intermediate directions between the respective directions.

It is possible to adopt, as other shapes, the shapes shown in FIGS. 9A, 9B, 9C, and 9D. These views show sectional shapes of the guide grooves 43 and wobbling prevention rollers 55, respectively. However, the guide grove 44 and the wobbling prevention roller 56 may adopt shapes symmetrical to the above shape with respect to the central axis of the C-arm 4 having the shape shown in each drawing.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A holding apparatus which holds an X-ray generator configured to irradiate an object with X-rays and an X-ray detector configured to detect X-rays transmitted through the object, the apparatus comprising:
    an arcuated arm provided with a guide groove along an outer surface, having a hollow portion inside, and configured to hold the X-ray generator and the X-ray detector, wherein the arm is provided with an opening portion, along the outer surface, which communicates with the hollow portion from the outer surface;
    a first roller configured to run in the hollow portion in abutment with an inner wall of the hollow portion which is located on the outer surface;
    a second roller configured to run in the guide groove while being fitted in the guide groove and hold the arm, together with the first roller, so as to allow the arm to slide along an arcuated direction of the arm;
    a frame inserted from the opening portion into the hollow portion, wherein the first roller is pivotally attached to a portion of the frame which is inserted into the hollow portion;
    a slide belt having two ends respectively fixed to end portions of the arm and stretched on the outer surface of the arm so as to close the opening portion; and
    a pair of slide belt rollers disposed on two sides of a portion of the frame which protrudes from the outer surface on a moving path of the portion and configured to press the slide belt against the outer surface of the arm.

2. The apparatus of claim 1, further comprising:
a driving member around which a portion of the slide belt which is located between the slide belt rollers is wound such that the slide belt straddles the portion protruding from the outer surface of the arm and which is configured to slide the arm along the arcuated direction by feeding the slide belt in either direction.

3. An X-ray diagnostic apparatus, comprising:
    an X-ray generator configured to irradiate an object with X-rays;
    an X-ray detector configured to detect X-rays transmitted through the object;
    an arcuated arm provided with a guide groove along an outer surface, having a hollow portion inside, and configured to hold the X-ray generator and the X-ray detector while making the X-ray generator and the X-ray detector squarely face each other, wherein the arm is provided with an opening portion, along the outer surface, which communicates with the hollow portion from the outer surface;
    a first roller configured to run in the hollow portion in abutment with an inner wall of the hollow portion which is located on the outer surface;
    a second roller configured to run in the guide groove while being fitted in the guide groove and hold the arm, together with the first roller, so as to allow the arm to slide along an arcuated direction of the arm;
    a frame inserted from the opening portion into the hollow portion, wherein the first roller is pivotally attached to a portion of the frame which is inserted into the hollow portion;
    a slide belt having two ends respectively fixed to end portions of the arm and stretched on the outer surface of the arm so as to close the opening portion; and
    a pair of slide belt rollers disposed on two sides of a portion of the frame which protrudes from the outer surface on a moving path of the portion and configured to press the slide belt against the outer surface of the arm.

4. The apparatus of claim 3, further comprising:
a driving member around which a portion of the slide belt which is located between the slide belt rollers is wound such that the slide belt straddles the portion protruding from the outer surface of the arm and which is configured to slide the arm along the arcuated direction by feeding the slide belt in either direction.

* * * * *